United States Patent [19]

Richards et al.

[11] Patent Number: 4,762,260
[45] Date of Patent: Aug. 9, 1988

[54] SURGICAL MICROSTAPLER

[75] Inventors: William D. Richards, Medway; Ernesto E. Blanco, Belmont; Richard A. Clark, Holliston; John C. Meade, Walpole, all of Mass.

[73] Assignee: Ophthalmic Ventures Limited Partnership, Norwood, Mass.

[21] Appl. No.: 906,151

[22] Filed: Sep. 11, 1986

[51] Int. Cl.$^4$ ............................................. A61B 17/00
[52] U.S. Cl. ........................................................ 227/19
[58] Field of Search .................... 227/19, DIG. 1, 93, 227/94, 95, 145, 196, 147, 120, 132

[56] References Cited

U.S. PATENT DOCUMENTS

| | | | |
|---|---|---|---|
| 1,568,260 | 1/1926 | Bates | 227/146 X |
| 2,174,708 | 10/1939 | Sears et al. | 227/95 X |
| 2,212,339 | 8/1940 | Cullen | 227/146 |
| 2,520,973 | 9/1950 | Sorenson | 227/93 |
| 2,767,399 | 10/1956 | Widener | 227/146 |
| 3,294,303 | 12/1966 | Anstett | 227/95 |
| 3,604,561 | 9/1971 | Mallina et al. | 206/56 DF |
| 3,646,801 | 3/1972 | Caroli | 227/DIG. 1 |
| 3,949,924 | 4/1976 | Green | 227/DIG. 1 |
| 4,014,492 | 3/1977 | Rothfuss | 227/132 X |
| 4,025,031 | 5/1977 | Chi | 227/132 |
| 4,162,678 | 7/1979 | Fedotou et al. | 227/DIG. 1 |
| 4,196,836 | 4/1980 | Becht | 227/DIG. 1 |
| 4,316,468 | 2/1982 | Klieman et al. | 227/DIG. 1 |
| 4,317,451 | 3/1982 | Cerwin et al. | 227/DIG. 1 |
| 4,410,125 | 10/1983 | Noiles et al. | 227/145 X |
| 4,485,816 | 12/1984 | Krumme | 227/DIG. 1 |
| 4,607,772 | 8/1986 | Ebihana | 227/120 |

Primary Examiner—Paul A. Bell
Attorney, Agent, or Firm—Schiller, Pandiscio & Kusmer

[57] ABSTRACT

A surgical microstapler is disclosed which does not require the use of a staple bending anvil that must be retracted after the staple is implanted. The surgical microstapler utilizes a stapler head comprising a staple magazine that consists of a series of staples attached to and supported by a plurality of frame members. The stables have a predetermined shape characterized by a spine portion and two opposite legs. The staples and frame members are formed as part of a sheet metal continuum and are joined by a plurality of tabs which coact with the frame members to hold the staples in proper spaced relationship within the magazine. The stapler head also comprises means for advancing the magazine so as to position its leading staple in a predetermined dispensing position in line with an ejection slot through which the staple is ejected and inserted into tissue, and staple driving means for implanting the leading staple. The leading staple is held to the magazine at its spine as it is engaged by the staple driving means. The staple driving means is shaped so as to contact the opposite legs of the staple and to deflect them downward following a curved trajectory with closely resembles the motion of a surgeon's suturing needle. The stapler head is adapted to be connected to a driver which provides the driving force required to cause the staple driving means to separate the leading staple from the magazine and implant it into the tissue.

34 Claims, 10 Drawing Sheets

SURGICAL MICROSTAPLER

FIELD OF THE INVENTION

This invention relates to new and improved apparatus for the suturing of delicate tissues by means of fine wire staples.

BACKGROUND OF THE INVENTION

Suturing is a very time-consuming phase of most surgical operations. Heretofore it has been realized that suturing time can be reduced considerably by the use of stapling techniques. As a consequence, in recent years several types of stapling systems have come into use for surgical suturing.

By way of example, the following U.S. patents illustrate the various types of staplers which have been used for suturing purposes: U.S. Pat. Nos. 3,604,561, 3,646,801, 4,162,678, 4,316,468, 4,317,451 and 4,485,816, and the references cited therein.

However, prior surgical stapling systems suffer from a variety of disadvantages, including but not limited to: (1) excessive size for the intended application; (2) the need to bend the staples across the tissues, which induces severe traumatic effects; (3) the need to extract the stapler anvil from the tissue surface after the staples have been implanted; and (4) inability to maintain precise edge alignment and smoothness as required in ophthalmic and cosmetic surgery. As a consequence, prior medical staplers have been unsuitable for delicate ophthalmic surgical operations where only an absolute minimum of trauma may be induced during the surgical procedure.

OBJECTS OF THE INVENTION

The present invention has as its primary object the provision of a stapler for the suturing of very delicate tissue incisions such as those involved in ophthalmic operations, neurosurgery, or plastic surgery.

A more specific object of the invention is to provide a new and improved surgical suturing microstapler system which is characterized by the use of very fine metallic staples made of a stainless steel alloy that is non-injurious to human tissues.

Another specific object of the invention is to provide a microstapler suturing system that is adapted to implant staples with a minimum of trauma, with the implanted staples providing at least the same holding strength as that obtainable with commonly used flexible filament sutures.

Still another object of the invention is to provide a surgical stapling system having pre-shaped staples which are held together in a magazine strip from which they are sheared cleanly after they have penetrated tissue so as to hold together the sides of an incision.

Still another object of the invention is to provide a microsurgical stapling system in which the staples are driven with a velocity in excess of the ability of live tissues to react dynamically under the force of the penetrating staples, so as to make it unnecessary to hold the limp edges of some delicate tissues at the time of stapling.

Still another object of the invention is to provide a stapler-type suturing system which is designed to suture together delicate tissues in a manner which reduces trauma to a minimum and assures proper incision alignment, as is essential for ophthalmic or plastic suturing where incision stresses can induce post-operative deformations such as astigmatism or scarring.

A further object of the invention is to provide a stapling system having staples which are shaped as close as possible to the atraumatic curvature best suited to reduce tissue pull and tear during penetration.

Still another object of the invention is to provide a microsurgical stapling system which does not require the use of a staple-bending anvil that must be retracted after the staple is implanted.

SUMMARY OF THE INVENTION

The foregoing and other objects (which are rendered obvious by the following detailed description) are achieved by a surgical suturing microstapler system which utilizes a unique staple magazine and a unique stapler head.

In the preferred embodiment of the invention, the staple magazine is formed from a stainless steel sheet and consists of a series of staples attached to and supported by a plurality of frame members. The staples are formed by die punching, chemical etching, or some other convenient method well known to persons skilled in the art. The staples have a predetermined shape characterized by a spine or body portion and two opposite legs. The staples and frame members are formed as part of a sheet metal continuum and are joined by a plurality of tiny tabs which coact with the frame members to hold the staples in proper spaced relationship within the magazine.

The new stapler head comprises means for holding and advancing the staple magazine so that the leading staple in the magazine is positioned in a predetermined dispensing position. The stapler head has an ejection slot through which a staple located in the predetermined dispensing position is ejected and inserted into the tissue to be sutured. The tool further includes staple driving means for engaging the leading staple and implanting it into the tissue through the ejection slot. The staple is held to the magazine at its spine as it is engaged by the staple driving means. The latter is shaped so as to contact the opposite legs of the staple and to deflect them downward following a curved trajectory inside the tissue. As the staple driving means continues advancing downward, causing the staple legs to be bent and to penetrate the tissue around an arc of trajectory which closely resembles the motion of a surgeon's suturing needle, the tabs are sheared against the edge of the ejection slot by portions of the staple driving means, freeing the staple from the magazine and leaving it implanted in the tissue. The unique shearing action of the new stapler system eliminates the need for an anvil.

Other features and advantages of the invention are described or rendered obvious by the following detailed description of a preferred embodiment of the invention, which is to be considered together with the accompanying drawings.

PREFERRED EMBODIMENT OF THE INVENTION

Referring now to FIGS. 1-7, there is shown a microsurgical stapling system comprising a manually operable driver 2 and a stapling tool or head 4 made in accordance with the present invention. Stapling head 4 comprises a tubular stem 6, a hollow housing 8 which contains most of the critical functioning parts of the head, and a curved laminar or leaf spring 10 for advancing a staple magazine or carrier strip 12 (FIG. 3) into position for dispensing the leading staple through an ejection slot formed in the bottom side of hollow housing 8.

As shown in FIGS. 1-7, hollow housing 8 is formed with a curved bottom wall 14 and opposite side walls 16 and 18, with those walls converging at the rear end of the hollow body to form a circularly-shaped channel section 20 that embraces and is welded or otherwise fastened to stem 6. A staple ejection slot 22 (FIG. 4) is formed in bottom wall 14. Hollow housing 8 also is provided with an internal bulkhead 24 that is attached to side walls 16 and 18 and terminates short of bottom wall 14.

Figure 2:
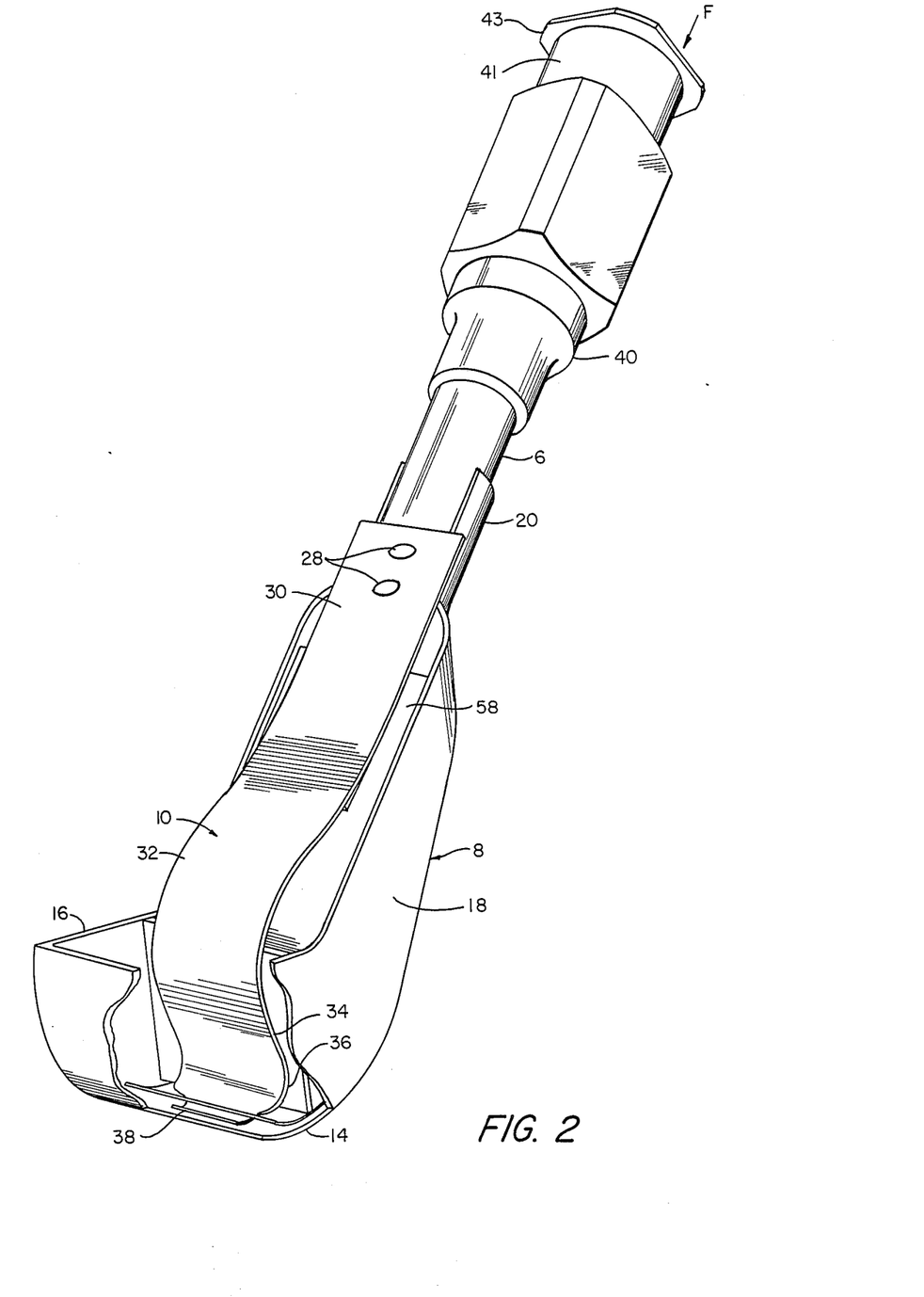
FIG. 2 is an enlarged perspective view of the same stapling head.
Figure 5:
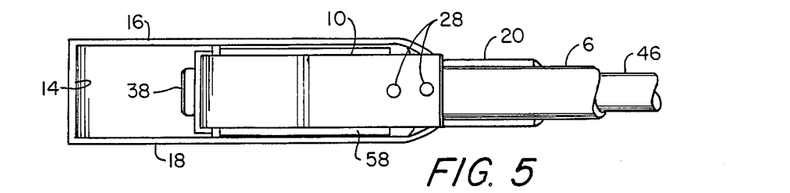
FIG. 5 is a plan view of the stapler head.
Figure 6:
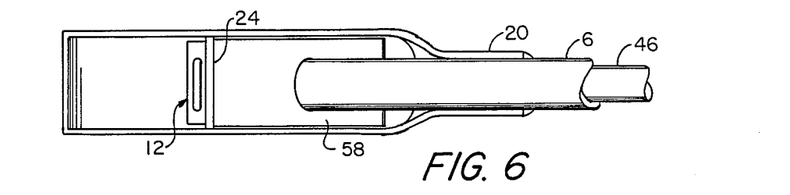
FIG. 6 is a plan view of the stapler head with the magazine feed spring member removed.
Figure 7:
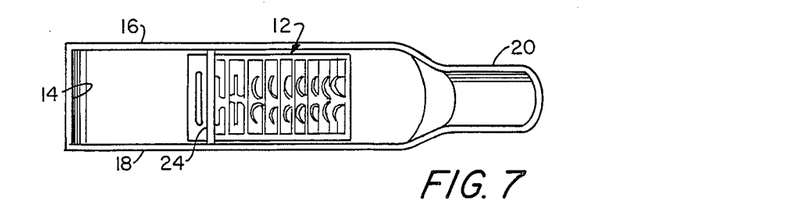
FIG. 7 is a further plan view of the stapler head with additional elements removed.

Preferably laminar spring 10 is attached to the hollow stem 6 through spot welds 28 (FIGS. 2 and 5). Spring 10 has an S-shaped curvature, comprising a relatively flat portion 30 which lies against the hollow stem 6, a convexly curved section 32 which curves away from the hollow housing 8, a nearly flat section 34 which extends down toward ejection slot 22, and a concavely curved section 36 which turns upwardly along bottom wall 14. The forward end of spring 10 is reduced in width to form a tang 38 which engages and moves the staple magazine 12 as hereinafter described.

Figure 1:
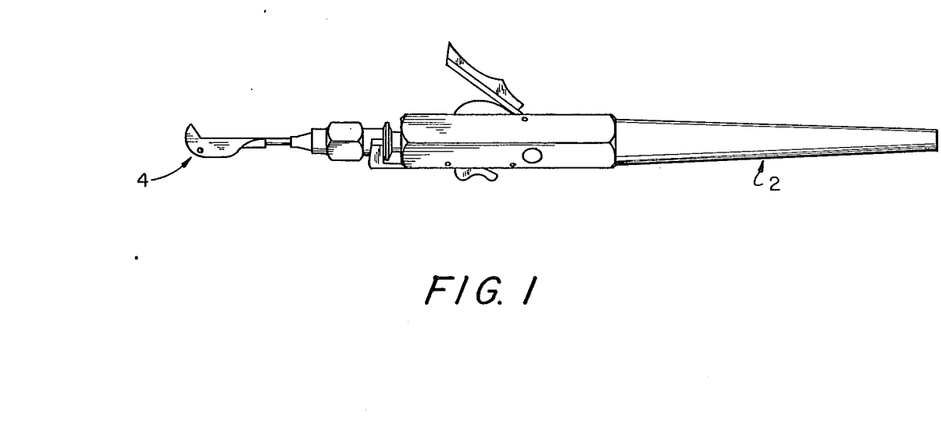
FIG. 1 is a side view in elevation of a stapling head made in accordance with this invention, in combination with a preferred driver.

Referring to FIGS. 1 and 2, hollow stem 6 has a hollow socket-like member 40 attached to its upper or outer end. The exterior of member 40 has a reduced diameter as shown at 41, resulting in a flange 43. The socket-like member 40 has a cylindrical axially-extending bore 42 which is counterbored as shown at 44. Bore 42 has the same diameter as the internal surface that defines axial bore 7 in stem 6. Slidably disposed within bores 7 and 42 is a plunger in the form of a ramrod 46. Adjacent its upper end the ramrod has a circular peripheral flange 48 sized to make a close sliding fit in counterbore 44. Captivated between flange 48 and the tapered bottom end 50 of counterbore 44 is a return coil spring 52. Spring 52 is a compression spring and acts to urge ramrod 46 in an upward direction, as viewed in FIG. 3.

Figures 17, 18:
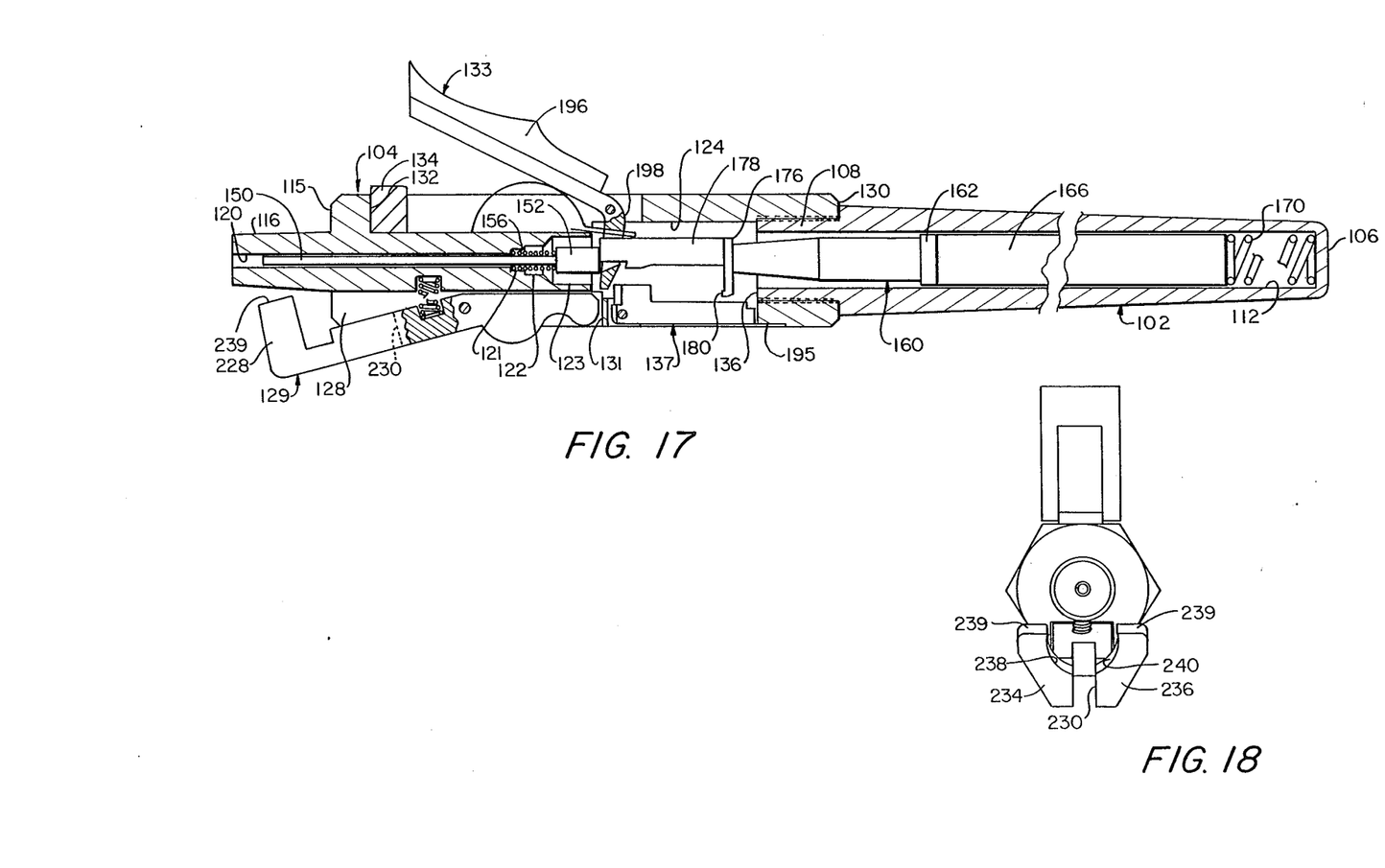
FIG. 17 is an enlarged longitudinal sectional view of the driver shown in FIG. 1.
FIG. 18 is an end view of the same driver.

Attached to socket-like member 40 is driver 2 for applying a driving force F (see FIGS. 2 and 3) to ramrod 46 against the force of return spring 52. Driver 2 may take various forms. Thus, as shown in FIGS. 17 and 18, it may be a trigger type mechanism in which an axial force F is derived from the discharge of a precocked spring released by operation of a trigger. However, other driver means could be used, e.g. a pneumatically or electrically-powered driver.

Figure 3:
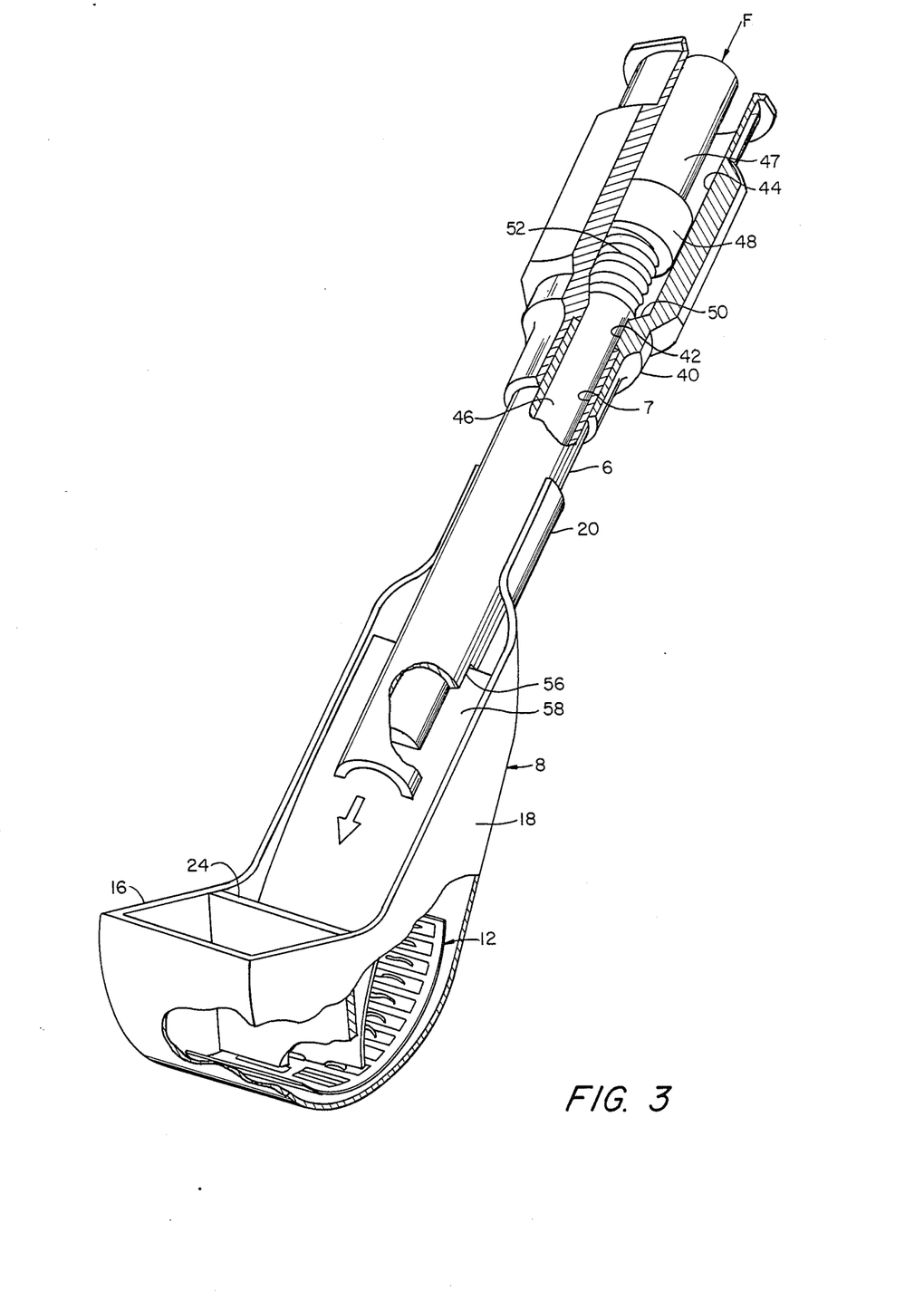
FIG. 3 is a view similar to FIG. 2, but with certain portions broken away, illustrating the disposition of the staple magazine within the stapler head.
Figure 4:
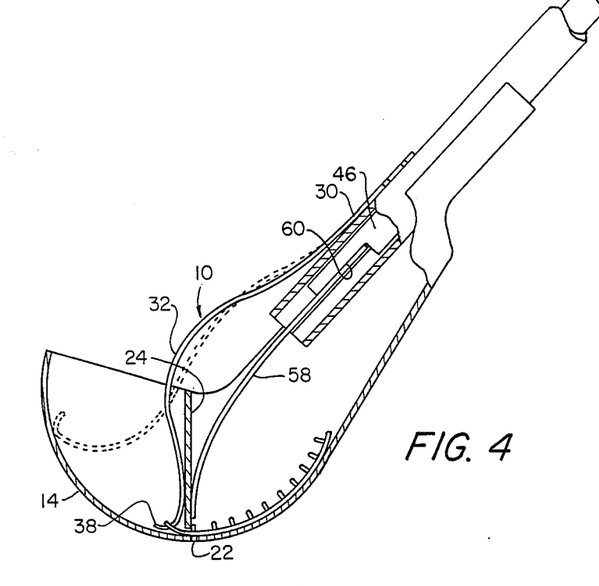
FIG. 4 is a side elevation, partly in section, illustrating the disposition of the staple magazine within the stapler head.

The bottom end of hollow tubular stem 6 extends into housing 8 and is slotted along a diameter as shown at 56 (FIG. 3) to accommodate a ram plate 58 that has a curvature as shown in FIG. 4 and is secured to the bottom end of ramrod 46. For this purpose, ramrod 46 has a flat recess 60 to accommodate the upper end of ram plate 58. The latter is welded or brazed to ramrod 46. As seen in FIGS. 2 and 3, ram plate 58 is wider than the outer diameter of stem 6, so that it projects from both sides of the diametrical slot 56. With this arrangement, rectilinear axial motion of ramrod 46 and ram plate 58 relative to stem 6 is permitted, while rotational axial motion of ramrod 46 relative to stem 6 is prevented by the interaction of ram plate 58 with the portions of stem 6 that define slot 56. Also the depth of slot 56 determines the extent of rearward motion of ram plate 58, since the edge surfaces of stem 6 that determine the depth of slot 56 act as a stop for ram plate 58.

As seen best in FIGS. 3 and 4, ram plate 58 is flat where it is attached to the ramrod, but its forward half is curved downwardly. The curvature of plate 58 is set so that its forward end (the bottom end as seen in FIG. 4) extends down at substantially a right angle to bottom wall 14 of housing 8. Also the ram plate is made long enough so that its forward end is substantially parallel to and engages bulkhead 24 when the ram plate is in its retracted position (FIG. 4).

Figure 10:
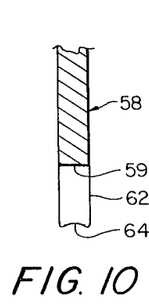
FIG. 10 is a fragmentary cross-sectional view taken along line 10-10 of FIG. 12 illustrating channels formed in the push lugs of ram plate 58.
Figure 12:
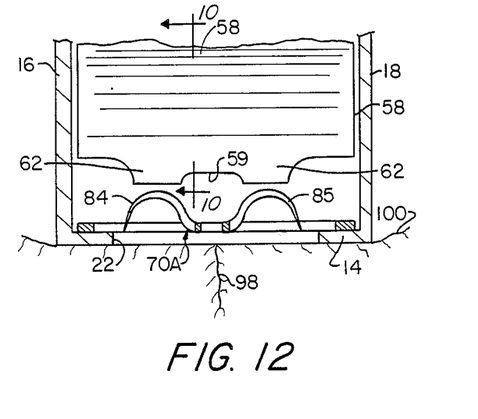
FIGS. 12, 14 and 16 are cross-sectional views, corresponding to FIGS. 11, 13 and 15 respectively, illustrating operation of the stapler head.

As seen best in FIG. 12, the bottom end of ram plate 58 is formed with two push lugs 62 that are spaced from one another. As seen in FIG. 10, the bottom edges of lugs 62 are formed with circularly-curved channels 64 to allow the lugs to conform to the shape of the top portions of the staples 70 hereinafter described. The purpose of channels 64 is to prevent the staple which is being driven from slipping out of contact with lugs 62.

Figure 8:
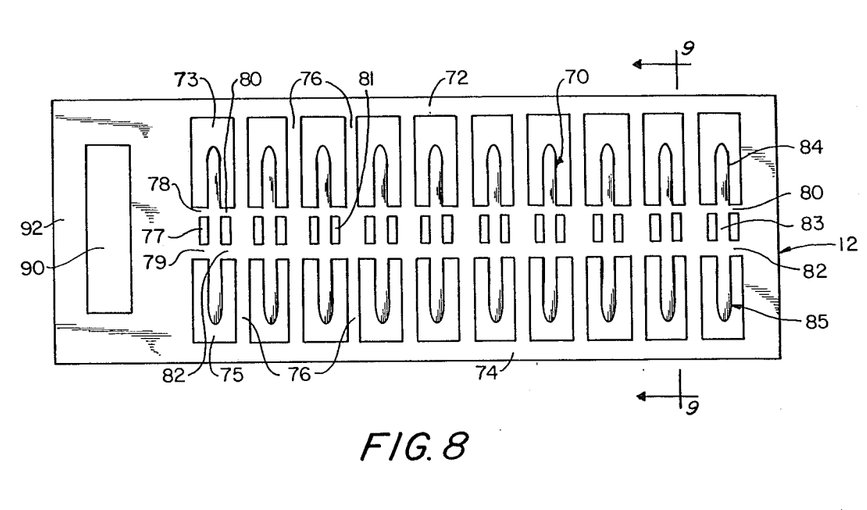
FIG. 8 is a plan view of a preferred form of staple magazine in an uncurved state.
Figure 9:
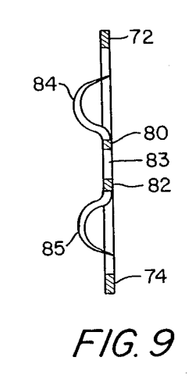
FIG. 9 is a sectional view of the staple magazine taken along line 9—9 of FIG. 8.

The staple magazine or carrier strip 12 is formed from a flat sheet of a suitable material, preferably stainless steel, and consists of a plurality of staples 70 formed in a suitable manner, e.g. by die punching and forming. As illustrated in FIGS. 8 and 9, the staples are part of a sheet continuum, each being disposed between side frame members 72 and 74 and cross frame members 76, and each having two tiny tabs 78 and 79 on one side joining it to cross frame members 76 and two tiny tabs 80 and 82 on its opposite side joining it to cross frame members 76. As seen in FIGS. 8, 9, 12, 14 and 16, staples 70 are formed with a body or spine portion 83 and two convexly curved legs 84 and 85 that project above the plane of staple magazine 12. The legs of staples 70 are formed so that they diverge slightly from one another, e.g. each leg extends at an angle of approximately 15-20 degrees to the vertical (see FIG. 9). Magazine 12 has openings 73, 75, 77 and 81 which assist in defining staples 70, frame members 72, 74 and 76, and tabs 78, 79, 80 and 82. Additionally, each staple magazine has a leading slot 90 that receives the forward end of spring 10, plus a leading end cross-member 92 that has a greater width than the cross frame members 76, in order to provide a better force distribution in response to the staple feeding action of spring 10. Tabs 78, 79, 80 and 82 may or may not be pre-sheared to facilitate proper separation of the staples 70 from magazine 12.

The elastic force of spring 10 serves to feed the magazine toward bulkhead 24 every time that the ram plate 58 is retracted after a staple has been implanted. Each operation of ram plate 58 causes the staple magazine to be advanced a distance equal to the spacing between successive staples, with return spring 52 causing ramrod 46 to return to its original position.

As seen in FIG. 4, when the ramrod 46 is in its relaxed or raised position, the push lugs 62 of ram plate 58 are in a retracted position relative to staple magazine 12.

The mode of operation of the system is illustrated in FIGS. 11-16.

Figure 11:
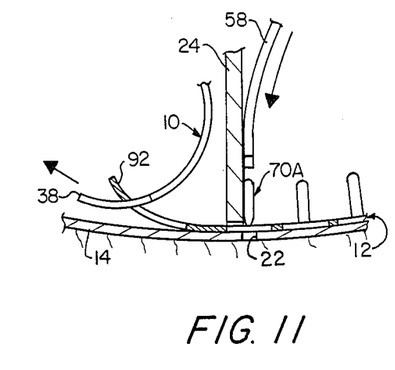
FIGS. 11, 13 and 15 are fragmentary longitudinal sectional views illustrating, operation of the new stapler head under the influence of the attached driver.
Figure 13:
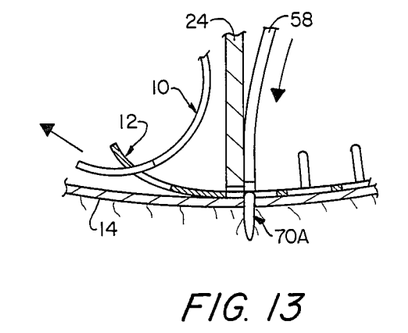
Figure 14:
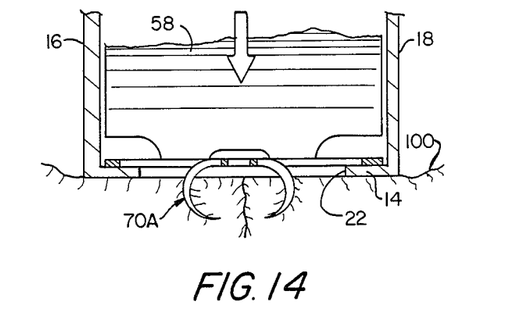
Figure 15:
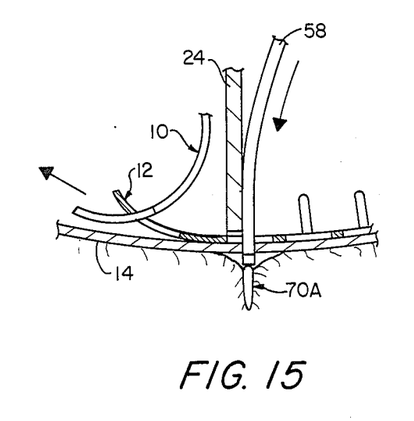
Figure 16:
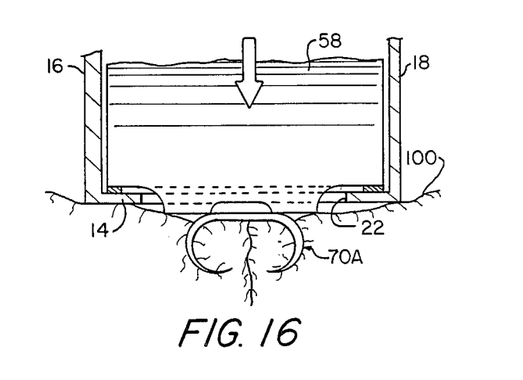

FIGS. 11, 13, and 15 provide a side view in elevation of selected elements of the system of FIGS. 1-9 in a typical surgical stapling operation, while FIGS. 12, 14, and 16 show a cross-sectional view of the same stapling operation. Referring first to FIGS. 11 and 12, the stapling head is shown positioned over an incision 98 in human tissue 100. At this time the stapling head is in its at-rest position which is characterized by the upper end of ram plate 58 being engaged with the upper end of slot 56 in stem 6 (FIG. 3) and the lower end of the same plate being engaged with bulkhead 24 but spaced from magazine 12 (FIG. 4). As seen in FIG. 12, the stapler is placed so as to straddle the incision to insure that the two legs 84 and 85 of the staple to be implanted will grasp approximately the same amount of tissue at each side of the incision. The staple to be implanted, i.e., the leading staple in the magazine, is labelled 70A in FIGS. 11-16 to differentiate it from the other staples of magazine 12. The lower end of ram plate 58 is located directly above the staple 70A that is to be implanted. Leaf spring 10 urges staple magazine 12 toward the left in FIG. 11, thereby feeding the leading staple toward the gap formed between bulkhead 24 and bottom wall 14 and holding that leading staple against the bulkhead in alignment with ejection slot 22. The staple magazine stays in this position until staple 70A is ejected, whereupon spring 10 will advance the magazine to place the next staple against the bulkhead after ram plate 58 has been retracted.

Assume that the surgeon now actuates driver 2 so as to cause ram plate 58 to be driven downwardly. As this occurs, ram plate push lugs 62 engage the upper portion of convexly curved legs 84 and 85 of staple 70A so that those portions reside in ram plate channels 64 (FIG. 10). Downward motion of ram plate 58 drives staple 70A downward so as to cause it to be sheared off from staple magazine 12. At the same time, push lugs 62 deflect the two convex legs 84 and 85 of the staple downward, with the legs following a curved trajectory as they are driven into the tissue on both sides of the incision. The engagement of channels 64 with the upper portions of legs 84 and 85 of staple 70A assures that the staple will not slide out from under ram plate lugs 62, whereby the staple is stabilized in the downward direction and prevented from squirming away from the control of ram plate 58 and its push lugs 62. The staple is guided during its downward motion by virtue of the fact that it remains engaged with bulkhead 24 until it is sheared off from its leading tabs 78 and 79 and its trailing tabs 80 and 82 (FIG. 8). As the staple moves down into and through ejection slot 22, downward movement of tabs 78, 79, 80 and 82 is impeded by the edge portions of bottom wall 14 that define ejection slot 22, with the result that further downward action of ram plate 58 causes those tabs to be sheared off from the staple. In this shearing action, the center portion 59 of the bottom end of ram plate 58 that extends between lugs 62 acts as a shear blade against the edges of ejection slot 22.

FIGS. 13 and 14 help illustrate what happens as ram plate 58 continues advancing downward, pushing staple 70A ahead of it. In these figures, staple 70A is shown as it undergoes maximum deformation, which occurs just before it is sheared off from the magazine. As seen in FIG. 14, the staple is deformed under the action of push lugs 62 so that its legs 84 and 85 follow an arc of trajectory as they penetrate the tissue. This action, which is similar to the motion of a surgeon's suturing needle, is beneficial since it reduces the possibility and/or degree of stitching trauma. FIGS. 13 and 14 show staple 70A almost fully implanted, with the two edges of the incision drawn firmly and evenly together, since they are both under the control of the bottom wall 14 of hollow body 8.

FIGS. 15 and 16 illustrate the final or shearing action. The downward stroke of ram plate 58 is limited, stopping when portion 59 of its bottom end has passed a short distance below the upper surface of bottom wall 14 at ejection slot 22, that distance being far enough below bottom wall 14 to sever tabs 78, 79, 80 and 82 by the shearing action previously described. Since the thickness of ram plate 58 (its width is its horizontal dimension as seen in FIGS. 11, 13 and 15) is only slightly less than that of slot 22, there is virtually no space or gap remaining between those elements as the shearing of tabs 78, 79, 80 and 82 occurs. It is to be noted that as it pushes and shears off staple 70A, ram plate 58 actually depresses the tissue surface (see FIG. 16) so as to facilitate a substantially firm and flush alignment between the staple and the portions of the tissue that border on the incision.

The result is a solution long sought by surgeons. The two legs of staple 70A move in a true, or nearly true, circular arc about the pivot points represented by tabs 78, 79, 80 and 82 which are not yet sheared. As a consequence those tabs provide stable and positive pivot points (as seen in FIGS. 12, 14 and 16), with most of the penetration and pressure-forming of the staple under the force of ram plate 58 occurring while the staple is still attached firmly to the staple magazine.

The result is virtually absolute control of the implantation of the staple and a minimization of trauma caused by improper alignment and/or direction of the implanted staple. It is to be appreciated that the present stapler also provides excellent control over the depth of penetration of the staple.

It is to be noted that at the time of implantation of a staple 70, the staple is inelastically deflected downward by ram plate 58. When the staples 70 are finally sheared off from the magazine, they have already begun to pull upwardly from the tissue due to the edge-gathering forces resulting from their curving entry into the tissue.

When a staple 70 is sheared off, its body or spine 83 will snap down against the surface of the tissue, thereby causing the staple to remain substantially flush with the tissue. When that occurs, the internal stresses imposed by the edge-gathering forces tend to disappear and incision 98 will remain perfectly closed but with a minimum of internal stressses and trauma.

The results and effects described above are obtained consistently and reliably with the present invention, in contrast with the great variability and uncertainty that characterizes present incision-closing techniques, especially those used in ophthalmology, where incision and suture sizes are extremely small and surgeons must depend on surgical microscopes for making and suturing incisions.

Turning now to FIGS. 1 and 17–20, there is shown a preferred form of driver 2 for operating the stapler described above. Driver 2 is designed to drive the staples with a velocity in excess of the ability of live tissues to react dynamically under the force of the penetrating staples, so as to make it unnecessary to hold and support the limp edges of some delicate tissues at the time of stapling.

Driver 2 comprises two hollow tubular bodies 102 and 104. Tubular body 102 is closed off at one end by an end wall 106 and has a reduced diameter forward end section 108 that is threaded as shown so that it may be screwed into a tapped hole in the adjacent end of second hollow body 104. Hollow body 102 has a constant diameter bore 112. Hollow body 104 has a forward end surface 115 and a reduced diameter hollow front extension 116. Hollow body 104 is characterized by a constant diameter axial bore 120 that extends from the forward end of its extension 116 and is transformed into four counterbores 121, 122, 123, and 124. The latter is threaded to mate with hollow body 102. Front extension 116 has an outer diameter such that it will make a snug sliding fit in counterbore 44 of the stapler head (FIG. 3), while bore 120 is sized so as to make a close sliding fit around the outer end 47 of ramrod 46.

The side wall of hollow body 104 is provided with an elongated flat-sided slot 128 for accomodating a clasp member 129. Slot 128 intersects forward end surface 115 and terminates a substantial distance short of the rear end surface 130 of hollow body 104 at a partition 131. Hollow body 104 has a second flat-sided slot 132 for accomodating a trigger member 133 and a trigger stop member 134. Slot 132 is located in diametric opposition to slot 128. Slot 132 extends from a point behind forward end surface 115 for approximately half the length of hollow body 104, and intersects counterbore 124. Hollow body 104 has a third slot 136 disposed in axial alignment with slot 128 for accommodating a pawl member 137. Slot 136 also intersects counterbore 124.

Disposed in bore 120 is a striker member 150. The latter has an enlarged head 152 having an outside diameter smaller than the diameters of counterbores 122 and 123. Surrounding striker member 150 is a compression spring 156 that urges the striker member toward counterbore 124. Spring 156 is engaged at one end with the shoulder formed by the junction of bore 120 and counterbore 121, while the opposite end of that spring engages head 152. Head 152 of striker 150 is engaged by the end of a ram member 160. Ram 160 has an enlarged head 162 at one end which engages a cylindrical inertia or weight member 166. The latter is engaged by a compression spring 170 that is disposed between weight 166 and the end wall 106, urging weight 166 away from end wall 106.

The forward end of ram 160 has a radially-extending finger 176 and an integral longitudinal extension 178, the latter being disposed eccentric to the center axis of the ram. Finger 176 has a catch 180 for engagement by a portion of pawl member 137, as hereinafter described. Ram extension 178 is notched as shown at 184 (FIG. 19) for engagement by a portion of trigger 133 as hereinafter described.

Figure 19:
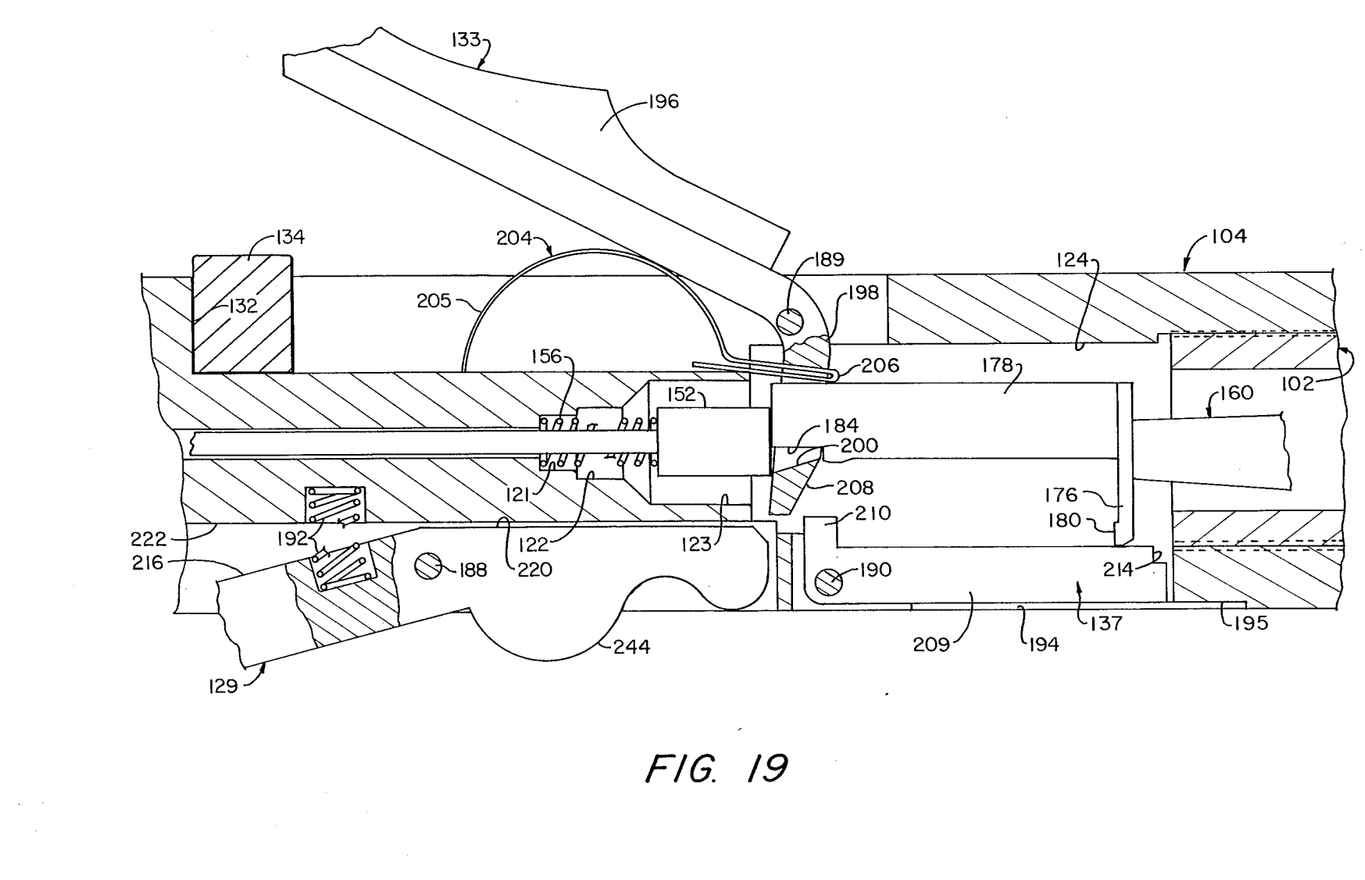
FIGS. 19 and 20 are enlarged fragmentary longitudinal sectional views illustrating operation of the driver.
Figure 20:
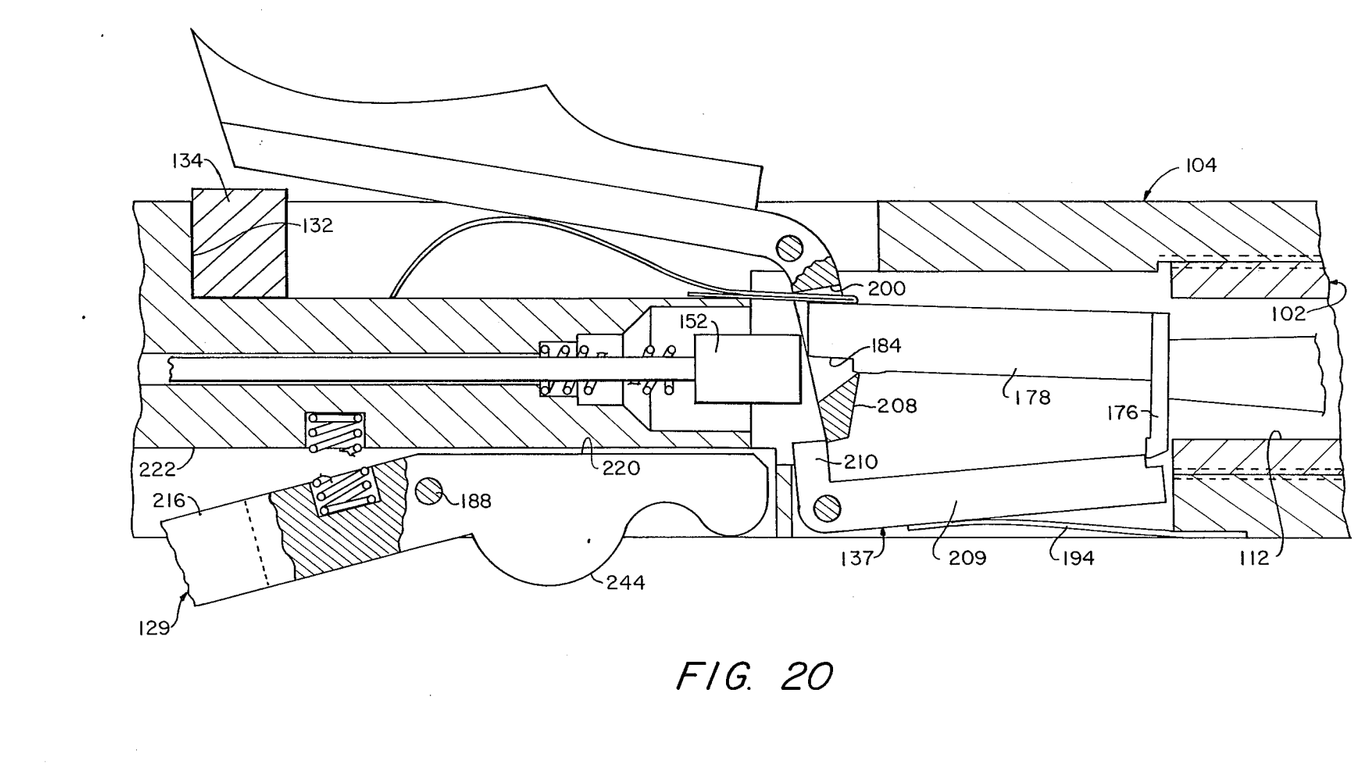

Clasp 129 is pivotally secured to hollow body 104 by a pivot pin 188 (FIG. 19), while trigger member 133 and pawl member 137 are pivotally attached to hollow body 104 by pivot pins 189 and 190, respectively. A compression spring 192, disposed in blind holes in clasp 129 and hollow body 104, urges the clasp to the open position shown in FIGS. 17, 19 and 20. Additionally a leaf spring 194 (FIG. 19) is brazed or welded in place in a shallow depression 195 in hollow body 104 that borders the slot 136. Leaf spring 194 bears against the long body portion 209 of pawl member 137 and urges it inwardly of the hollow body, i.e., so that it is urged in a counterclockwise direction as seen in FIGS. 17, 19 and 20.

Trigger 133 is generally L-shaped, comprising a first surgeon-engageable portion 196 and a ram actuating portion 198. Ram actuating portion 198 is provided with a hole 200 (FIG. 19) which is sized so as to make a loose fit with ram extension 178. A contoured leaf spring 204 has a first end portion 205 which engages the bottom of slot 132, and a folded back portion 206 which extends into hole 200 of trigger 133 and simultaneously engages the bottom surface of slot 132. The folded back portion 206 of spring 204 bears against the exterior surface of ram extension 178 so as to urge it downwardly (as viewed in FIGS. 17, 19 and 20) toward pivot pin 190. The ram engaging portion 198 of trigger 133 is provided with a bevelled surface 208 which faces finger 176.

Pawl member 137 comprises a long body portion 209 having a lateral extension 210 adjacent pivot pin 190. Lateral extension 210 extends adjacent to the bevelled surface 208 of trigger 133 when the latter and pawl member 137 are disposed in the driver's at-rest position shown in FIG. 19. Pawl member 137 also has a notch 214 at its free end for the purpose of making engagement with the catch portion of finger 176 when the driver is placed in cocking condition, as hereinafter described.

Clasp 129 has a surface 216 which extends at an angle to a surface 220, both of said surfaces being flat for engagement with the flat surface 222 that forms the bottom of slot 128. Engagement of surface 220 with surface 222 determines the open position of the clasp member, while engagement of surface 216 with surface 222 determines the closed position of the clasp member.

At its free or forward end clasp member 129 is provided with a right angle extension 228 (FIG. 17) and also is slotted as shown at 230 (FIGS. 17 and 18), whereby the forward end of the clasp member, including its right angle extension 228, is divided into two arms 234 and 236. The inner surfaces of arms 234 and 236 are contoured so as to have circularly curved confronting surfaces 238 and 240. The radius of curvature of each of the surfaces 238 and 240 is substantially the same as that of the exterior of surface 41 of socket-like member 40 (FIG. 2). Surfaces 234 and 236 extend far enough to be mutually converging where they intersect the flat end surfaces 239 of the free ends of the two arms, i.e., the end surfaces 239 of the free forward extremities of arms 234 and 236 are spaced from one another a distance less than the radius of curvature of surfaces 238 and 240.

The stapler head of FIGS. 1–10 is attached to the driver by inserting the driver's tubular extension 116 (FIG. 17) into axial counterbore 44 of the stapler's socket-like member 40 (FIG. 3). The socket-like member 40, its counterbore 44, striker 150 and extension 116 have lengths such that when extension 116 is inserted into socket-like member 40, striker 150 will lightly contact ramrod 46 and flange 43 will be spaced from end surface 115 of driver 2. Thereafter clasp 129 is pivoted clockwise as seen in FIG. 17, forcing its arms 234 and 236 to engage the circularly-curved outer surface 41 of the stapler head. Because arms 234 and 236 are resilient, under the pivoting force they will spring apart to pass around the reduced diameter section 41 of the stapler head. The resiliency of arms 234 and 236 then will automatically cause them to compress against outer surface 41, locking the stapler head to the driver. Removal of the stapler head from the driver is achieved by the operator's pressing of bump or projection 244 (FIG. 19), which in turn will cause clasp 129 to pivot counterclockwise (as viewed in FIGS. 17 and 19) out of contact with socket-like member 40.

Operation of the driver will now be described.

Assuming that the stapling head of FIGS. 1–10 is mounted on the front end of driver 2 and locked in place by clasp 129, the driver is cocked by depressing trigger 133 once, i.e., pivoting it counterclockwise as seen in FIG. 17, until it engages trigger stop member 134. As trigger 133 is depressed, its extension 198 engages the shoulder formed by notch 184 in ram extension 178 and forces ram member 160 to the right (as seen in FIGS. 17, 19 and 20), forcing inertia weight 166 to compress spring 170. Ram 160 is moved to the right far enough to position finger 176 beyond notch 214 in pawl 137, whereupon leaf spring 194 will force pawl 137 to pivot counterclockwise (as seen in FIG. 17) inwardly far enough for notch 214 of pawl 137 to engage catch 180 of ram member 160. Thereafter, when trigger 133 is released, spring 170 will urge ram member 160 to the left (as seen in FIG. 17), causing pawl 137 to pivot counterclockwise about its pivot pin 190 until extension 210 engages partition 131, whereupon ram 160 moves out of alignment with the internal oversized bore 112 of hollow body 102, unhooking trigger portion 198 from ram notch 184 (as used in this context, "out of alignment" means that the left hand end of ram member 160 is shifted upwardly in FIGS. 17, 19 and 20). At the same time, the free end of the portion 198 of trigger 133 will have intruded behind and be locked by the lateral extension 210 of pawl 137 (FIG. 20).

At this point the forward end of ram extension 178 may or may not be engaged by head 152 of striker 150, depending on the axial position of striker 150. In any case, it is to be appreciated that spring 156 does not actively bias striker head 152 against the retracted ram extension. See FIG. 20.

Firing of the cocked driver is achieved by depressing trigger 133 a second time. When this occurs, the lateral portion 198 of trigger 133 will force ram member 160 further out of alignment with the oversized bore 112 of hollow body 102, i.e., the extension 178 of ram member 160 is moved further upwardly against folded back portion 206 of spring 204 (as seen in FIGS. 17, 19 and 20), thereby disengaging catch 180 from the notched portion 214 of pawl member 137, whereupon the ram will be driven forward by inertia weight 166 acting under the force of spring 170. As a consquence, ram extension 178 will impact against head 152 of striker 150, driving the latter forward along bore 120. As it is propelled forward, striker 150 will engage ramrod 46 of the stapler head, causing the ramrod to drive ram plate 58 downwardly to cause a staple to be discharged in the manner previously described.

At the same time forward movement of ram member 160 will cause its finger 176 to slide along the inner surface of pawl 137, thereby camming pawl 137 in a clockwise direction (when viewed from the direction of FIGS. 17, 19 and 20) back to its original at-rest position, whereby on release of trigger 133, the trigger's lateral extension 198 is free to swing back to the position shown in FIGS. 17 and 19 without interference by the lateral extension 210 of pawl 137. At this point driver 2 is ready to be cocked again in preparation for implanting of another staple.

The driver shown in FIGS. 17–20 offers the advantage that it is compact, easy to hold and use, and can be arranged to cause ram plate 58 to drive staples 70 with a velocity substantially in excess of the ability of live tissues to react dynamically under the force of the penetrating staples, so as to make it unnecessary to hold together the limp edges of delicate tissues at the time of stapling. The latter advantage is very significant when using the stapling system to suture sensitive tissue, e.g. in ophthalmic or cosmetic surgery procedures. Further advantages are that the staples are positively positioned in line with ejection slot 22, thereby reducing the possibility of jamming or misfiring, and the stapler head is easily replaced by a new one when its supply of staples has been exhausted.

MODIFICATIONS OF THE PREFERRED EMBODIMENT

Obviously the apparatus herein described may be modified in various ways without departing from the essential principles of the invention. Thus the number of tabs holding each staple 70 to the surrounding frame members may be varied, so that, for example, each staple may be held at its leading or trailing side by one, two or more tabs, and the number of tabs on one side may or may not be equal to the number of tabs on the opposite side. Similarly, the number of staples in the magazine may be varied.

Figure 9A:
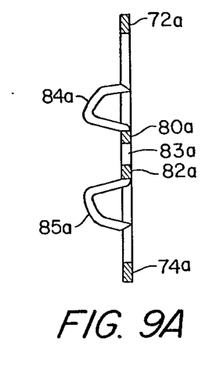
FIG. 9A is a sectional view of an alternative form of staple magazine, illustrating an alternative staple design.

It is also contemplated that the shape of the staples may be varied somewhat from that shown in FIG. 9. Thus, while the staples generally comprise a substantially straight body section and a pair of curved legs, it is possible to form the legs with something other than a "continuous" curvature. FIG. 9A illustrates such an alternative staple design. More specifically, the staple shown in FIG. 9A is identical to the staple shown in FIG. 9, except that each of the legs 84a, 85a of the staple of FIG. 9A is distinctly bent at two different points along the length of the leg, rather than being more or less "continuously" rounded as is the case with the legs of the staple of FIG. 9. The staple of FIG. 9A has been found to set itself flatter against certain types of body tissue that the staple of FIG. 9 in certain circumstances. It is to be appreciated that it is also possible to form the staple so that each of the legs of the staple is distinctly bent at only one point along the length of the leg, or is distinctly bent at more than two points along the length of the leg.

Furthermore, while the stapler head shown is designed to be discarded when all of the staples in magazine 12 have been used, it is contemplated that the stapler head may be modified to provide for replacing an empty magazine with a full magazine 12. Also a driver different from driver 2 may be used with the stapling head of this invention.

Figure 21:
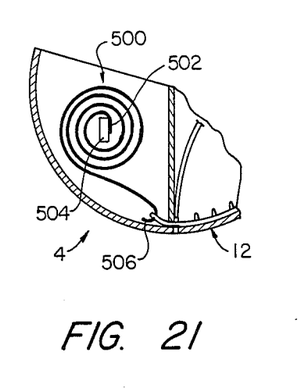
FIG. 21, is a partial side elevation, partly in section, illustrating an alternative form of stapler head.

Furthermore, the manner of advancing staple magazine 12 within stapler head 4 may be changed. Thus, for example, leaf spring 10 may be replaced by a coil spring 500 (FIG. 21) which has its interior end 502 attached to a crossbar 504 which extends between the stapler head's opposite side walls 16 and 18 (FIG. 2) and which has its exterior end 506 attached to the leading end of staple magazine 12.

It is also to be appreciated that the relative positions of spring 170 and weight 166 may be reversed, i.e., so that weight 166 engages end wall 106 and spring 170 engages the enlarged head 162 of ram 160. Such a construction will reduce the inertia to be overcome by spring 170 when driving ram 160 forward, thereby allowing the ram (and hence the staple) to be driven at a higher velocity.

Still other advantages, modifications and uses will be obvious to persons skilled in the art.

What is claimed is:

1. A surgical stapling system for driving a staple into human or animal tissue, said system comprising:
    (A) a stapling mechanism, and
    (b) a staple carrier strip, said staple carrier strip comprising a frame and a plurality of staples attached to said frame, each of said staples having a body section and a pair of legs extending from opposite sides of said body section, said body section being attached to said frame by at least one tab leading said body section and at least one tab trailing said body section, said legs extending perpendicular to the plane of said frame so that said legs protrude above said frame, said two legs having ends that are adapted to pierce said tissue;
    said stapling mechanism comprising:
    a wall having a stape ejection slot;
    means for advancing said staple carrier strip along said wall so as to position the leading staple in alignment with said staple ejection slot;
    first means for engaging the two legs of said leading staple and driving the two legs thereof downwardly through said ejection slot into tissue engaged by said first wall; and
    second means for severing said leading staple from said staple carrier strip and driving it through said ejection slot.

2. A system according to claim 1 wherein said legs have pointed ends that extend at acute angles to said frame.

3. A system according to claim 1 wherein said legs have free ends that terminate substantially in the plane of said frame.

4. A system according to claim 1 wherein said legs have free ends that are oriented in diverging relation to each other.

5. A system according to claim 1 wherein said first means comprises a pair of lugs formed on a ram palte, and said second means comprises edge portions of said ram plate.

6. A system according to claim 1 wherein said staple carrier strip has a slot therein, and said means for advancing said staple carrier strip along said wall comprises a member that projects into said slot.

7. A system according to claim 1 wherein said first and second means operate sequentially in the order named.

8. A system according to claim 1 wherein said stapling mechanism comprises a second wall extending at an angle to said first-mentioned wall, said second wall being adjacent to said ejection slot, whereby when said staple carrier strip is advanced along said first-mentioned wall, said leading staple in said staple carrier strip will engage and be stopped by said second wall in alignment with said staple ejection slot.

9. A system according to claim 8 comprising a ram plate and means for reciprocating said ram plate along said second wall into and out of said ejection slot.

10. A stapling system according to claim 9 wherein said ram plate has a bottom end, and further wherein said first means comprises a pair of push lugs formed on said bottom end of said ram plate, and said second means comprises edge surfaces on said bottom end of said ram plate.

11. A stapling system according to claim 10 wherein said ram plate is movable from a first limit position to a second limit position, and further wherein said bottom end of said ram plate protrudes through said ejection slot when said ram plate is in said second limit position and is spaced from said first-mentioned wall when said ram plate is in said first limit position.

12. A surgical stapling system for driving a staple into human or animal tissue, said system having a stapling head that comprises:
    a wall having a staple ejection slot;
    a multi-staple staple carrier strip extending along and engaged with said wall, said staple carrier strip comprising a frame and a plurality of parallel staples formed integrally with said frame, each of said staples comprising two leg portions and a spine portion connecting said two leg portions, each of said staples being attached to said frame by at least one tab leading said spine portion and at least one tab trailing said spine portion, said leg portions extending upward perpendicular to the plane of said frame so that said legs protrude above said frame;
    means for advancing said staple carrier strip one staple at a time along said wall so as to position the leading staple in said staple carrier strip in alignment with said ejection slot;
    means for severing said leading staple from said staple carrier strip and driving it through said ejection slot into tissue on both sides of a surgical incision; and
    means associated with said severing means for engaging said two leg portions of said leading staple and transforming said two legs so that said legs move in a nearly circular arc as said leading staple is driven through said ejection slot into said tissue.

13. A surgical stapling system for driving a staple into human or animal tissue, said system comprising:
    (a) a stapling head, and
    (b) a staple carrier strip, said staple carrier strip comprising a frame and a plurality of staples attached to said frame, each of said staples having a body section and a pair of legs extending from opposite sides of said body section, said body section being attached to said frame by at least one tab leading said body section and at least one tab trailing said body section, said legs extending upward perpendicular to the plane of said frame so that said legs protrude above said frame, said legs having ends that are adapted to pierce tissue;

said stapling head comprising:

a first wall having a staple ejection slot;

a second wall extending at an angle to said first wall;

means for urging said staple carrier strip to advance along said first wall and for causing the leading staple in said staple carrier strip to engage and be stopped by said second wall; and reciprocably movable means having (1) first means operative when said reciprocably movable means is driven in a first direction for engaging the two legs of said leading staple and driving the two legs thereof downwardly along said second wall and through said ejection slot into human or animal tissue engaged by said first wall, and (2) second means operative when said reciprocably movable means is driven in said first direction for severing said tabs so as to detach said body section of said leading staple from said staple carrier strip and driving it through said ejection slot so as to lie tight against said tissue after said legs have penetrated said tissue.

14. A surgical stapling system according to claim 13 further including a selectively operable stapling head driver connected to said stapling head, said driver comprising a driver member for engaging said reciprocably movable means and driving said reciprocably movable means in said first direction, and selectively operable means for causing said driver member to engage and drive said reciprocably movable means in said first direction.

15. A surgical stapling system according to claim 14 wherein said selectively operable driver comprises movable inertia means for impacting said driver member so as to cause said driver member to engage and drive said reciprocably movable means in said first direction, and means for controlling movement of said movable inertia means.

16. A surgical stapling system according to claim 15 wherein said stapling head driver is manually operated.

17. A surgical stapling system according to claim 16 wherein said selectively operable means comprises a trigger, and means (a) operative when said trigger is actuated a first time for positioning said movable inertia means in a selected position in which potential energy is stored and (b) operative when said trigger member is actuated a second time for releasing said potential energy so as to cause said inertia means to move rapidly from said selected position in a direction to impact said driver member and thereby cause said driver member to drive said reciprocably movable means in said first direction.

18. A surgical stapling system according to claim 14 wherein said stapling head driver is releasably attached to said stapling head.

19. A surgical stapling system according to claim 14 wherein said stapling head driver has a mode of operation characterized by a first cocking condition and a second driving condition, and further wherein said stapling head driver has a trigger and means responsive to movement of said trigger for (a) placing said stapling head driver in said first cocking position on a first movement of said trigger, and (b) firing said stapling head driver on a second movement of said trigger.

20. A multi-staple staple carrier strip formed from a sheet of a selected metal, said staple carrier strip comprising:

a pair of side frame members and a plurality of cross-frame members extending between and attached to said side frame members;

a plurality of staples each disposed between said side frame members and a pair of said cross-frame members; and a plurality of tabs extending between and attached to said staples and said cross-frame members, whereby said staples are mounted in a fixed spatial relationship to said cross-frame members.

21. A staple carrier strip according to claim 20 wherein said staples have a body section and a pair of legs extending from opposite sides of said body section, said legs extending in a plane perpendicular to the plane of said frame so that said legs protrude from said frame.

22. A staple carrier strip according to claim 21 wherein each staple's body section extends parallel to said cross-frame members.

23. A staple carrier strip according to claim 22 wherein said cross-frame members reside in a common plane.

24. A staple carrier strip according to claim 22 wherein each leg section is curved in a plane extending at a right angle to said common plane.

25. A staple carrier strip according to claim 24 wherein each leg section is circularly curved.

26. A staple carrier strip according to claim 22 wherein said pair of leg sections have pointed ends, and said pointed ends are disposed in diverging relation to one another.

27. A staple carrier strip according to claim 22 wherein each body section is disposed between two parallel cross-frame members and is attached to each of said two parallel cross-frame members by two mutually spaced tabs.

28. A staple carrier strip according to claim 22 wherein each body section is disposed between two parallel cross-frame members and is attached to one of said two cross-frame members by one of said tabs and to the other of said two cross-frame members by two of said tabs.

29. A staple carrier strip according to claim 22 wherein each body section is disposed between two parallel cross-frame members and is attached to each of said two cross-frame members by a single one of said tabs.

30. A staple carrier strip according to claim 20 wherein said tabs have a thickness less than the thickness of said cross-frame members and the thickness of said staples.

31. In combination with a stapler head that has a staple carrier strip comprising a plurality of staples and a reciprocably movable staple ram plate for separating a staple from said staple carrier strip and driving said staple into a selected work piece, a staple head driver releasably attached to said stapler head, said staple head driver comprising:

(a) a reciprocably movable means for driving said ram plate in a first direction toward said staple carrier strip;

(b) selectively operable means including a trigger means for causing said reciprocably movable means to move from a first retracted position to a second extended position so as to drive said ram plate in said first direction so as to sever a staple from said staple carrier strip; and (c) means for causing said reciprocably movable means to return from said second extended position to said first retracted position.

32. A multi-staple strip formed from a sheet of a selected metal, said strip comprising:

a pair of side frame members and a plurality of cross-frame members extending between and attached to said side frame members, said side frame members and said cross-frame members residing in a common plane;

a plurality of staples each disposed between and spaced from said side frame members and a pair of said cross-frame members; and at least one tab extending between each side of each staple and an adjacent cross-frame member, said tabs being formed integral with said staples and said cross-frame member and serving to support said staples in a fixed spatial relationship to said cross-frame members.

33. A strip according to claim 32 wherein each staple comprises a body section and a pair of leg sections extending parallel to said cross-frame members and projecting from said common plane.

34. A strip according to claim 33 wherein each leg section is curved in a plane extending at a right angle to said common plane.

* * * * *

UNITED STATES PATENT AND TRADEMARK OFFICE
CERTIFICATE OF CORRECTION

PATENT NO. : 4,762,260

DATED : August 9, 1988

INVENTOR(S) : William D. Richards et al.

It is certified that error appears in the above-identified patent and that said Letters Patent is hereby corrected as shown below:

Claim 1, col. 11, line 45, the term "stape" should be changed to the word -- staple --;

Claim 5, col. 11, line 66, the term "palte" should be changed to the word -- plate --; and Claim 17, col. 13, line 52, a comma should be inserted after the word "stored" and before the word "and".

Signed and Sealed this

Tenth Day of January, 1989

Attest:

DONALD J. QUIGG

*Attesting Officer*     *Commissioner of Patents and Trademarks*